United States Patent
Tufts et al.

(10) Patent No.: US 7,422,388 B2
(45) Date of Patent: *Sep. 9, 2008

(54) APPLICATOR FOR COLORING ANTISEPTIC

(75) Inventors: Scott A. Tufts, El Paso, TX (US); Jesus Flores, El Paso, TX (US); Manuel Guzman, El Paso, TX (US)

(73) Assignee: Allegiance Corporation, McGaw Park, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/739,918

(22) Filed: Apr. 25, 2007

(65) Prior Publication Data

US 2007/0248399 A1  Oct. 25, 2007

Related U.S. Application Data

(63) Continuation of application No. 11/254,318, filed on Oct. 20, 2005, now Pat. No. 7,241,065, which is a continuation of application No. 10/796,759, filed on Mar. 9, 2004, now Pat. No. 6,991,393, which is a continuation of application No. 10/388,826, filed on Mar. 14, 2003, now Pat. No. 6,729,786.

(51) Int. Cl.
*B43K 5/14* (2006.01)
*B43K 5/00* (2006.01)
*A61M 35/00* (2006.01)

(52) U.S. Cl. .................. 401/133; 401/132; 401/205; 604/3

(58) Field of Classification Search ............ 401/40–42, 401/132–135, 196, 205; 604/1–3
See application file for complete search history.

(56) References Cited

U.S. PATENT DOCUMENTS 6,027,271 A * 2/2000 Barosso et al. ................ 401/40
6,283,933 B1 * 9/2001 D'Alessio et al. .............. 604/3

* cited by examiner

*Primary Examiner*—David J Walczak
(74) *Attorney, Agent, or Firm*—Arent Fox LLP

(57) ABSTRACT

Applicators and a method of coloring antiseptics are provided. More specifically, in one embodiment, an applicator having a flexible hollow body containing antiseptic to be applied is provided. The applicator also has a porous element containing colorant positioned such that the antiseptic flows through the porous element containing colorant. Colorant is transferred to the antiseptic as it flows through the porous element. The resulting colored solution may be applied to the desired surface.

20 Claims, 3 Drawing Sheets

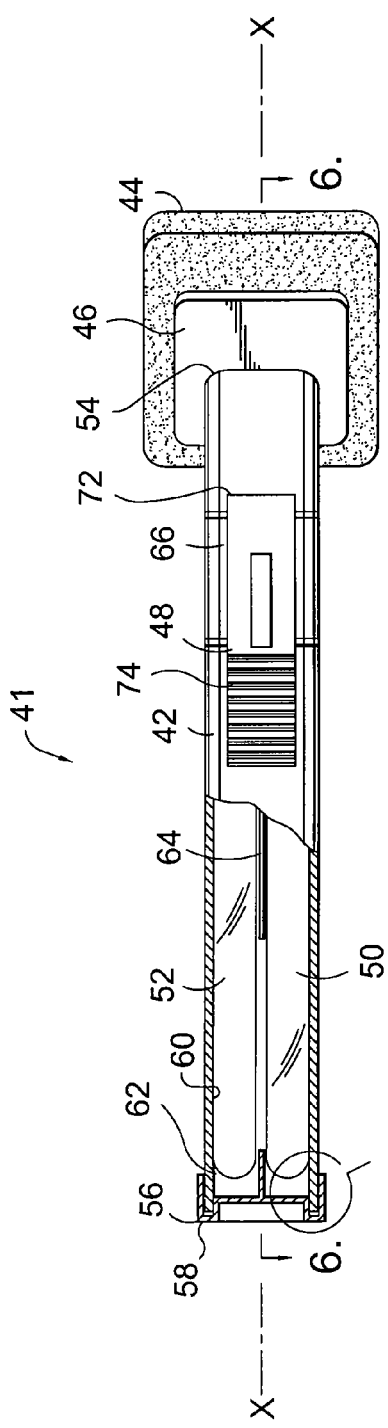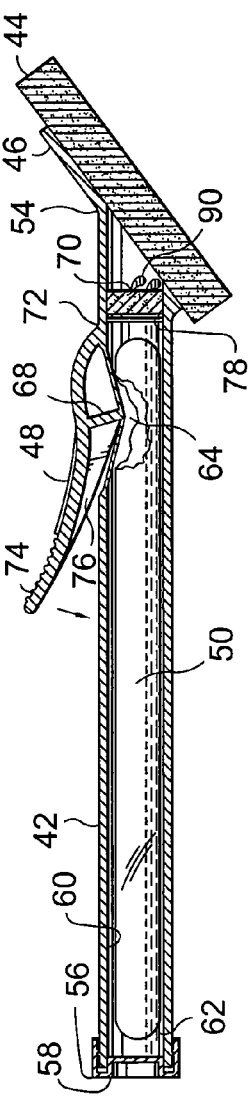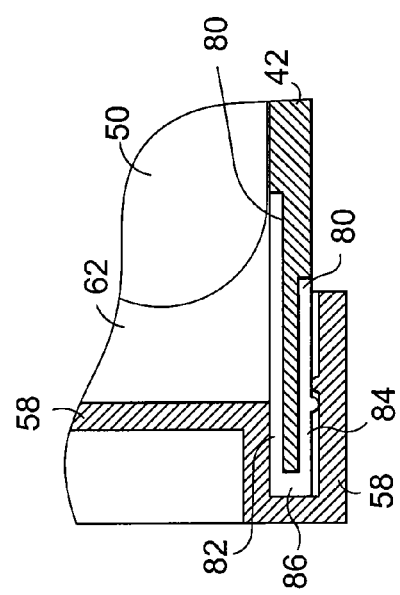

APPLICATOR FOR COLORING ANTISEPTIC

CROSS-REFERENCE TO RELATED APPLICATIONS

The application is a continuation application of U.S. patent application Ser. No. 11/254,318, now U.S. Pat. No. 7,241,065, filed on Oct. 20, 2005, which is a continuation application of U.S. patent application Ser. No. 10/796,759, now U.S. Pat. No. 6,991,393 filed on Mar. 9, 2004, which is a continuation application of U.S. patent application Ser. No. 10/388,826, now U.S. Pat. No. 6,729,786 filed on Mar. 14, 2003.

STATEMENT REGARDING FEDERALLY SPONSORED RESEARCH OF DEVELOPMENT

Not Applicable.

BACKGROUND

Applicators for applying liquids such as medicaments or cleansing agents are known in the prior art. Conventional applicators typically provide a generally cylindrical body construction and include a glass ampoule retained within the body; a sponge or tip secured to the body, at least one surface of which is exposed to the ampoule; and a means for fracturing the ampoule such that when the ampoule is fractured, the liquid stored therein is dispensed to the sponge for application.

When a non-colored or clear liquid is applied using these applicators, it is difficult for the user to see where the liquid has been applied. Thus, in many situations, it is necessary to utilize colored liquid so that the user knows where the liquid has been applied. For example, antiseptics or medicaments used as a pre-operative liquid are applied to the body just prior to surgery. It is essential that the user be able see where the pre-operative liquid has been applied. If the pre-operative liquid is colored, it is easier for the user to discern where the liquid has been applied to the body.

However, it is difficult to apply a colored liquid using these applicators. Numerous problems are encountered when color, such as a tint or dye, is added to a liquid using an applicator of this type. For example, when a tint or dye is added to a liquid, the shelf life of the liquid may be shortened and/or the colored solution may become unstable. A further problem is colorant may settle out of the liquid. If colorant settles out of the liquid there may be non-uniform distribution of the colored liquid when applied.

SUMMARY

The present invention provides a liquid applicator for applying a desired liquid to a surface, the applicator comprises: at least one ampoule formed of a frangible material and adapted to contain liquid to be applied; at least one hollow body defining an internal chamber adapted to receive at least one ampoule; and at least one porous element that contains colorant, wherein the porous element may be a porous plug located between the ampoule and the open end of the body and/or the porous element may be a porous pad closing off an open end of the body, and wherein the porous element is positioned such that liquid flows through the porous element when at least one ampoule is fractured and colorant is transferred to the liquid to be applied.

The present invention further provides a method of making a porous plug containing colorant. The method comprises mixing water, dye and isopropyl alcohol, saturating the porous plug with the mixture and allowing the porous plug to dry.

Accordingly, the present invention further provides a liquid applicator for applying a desired liquid to a surface, the applicator comprises: at least one ampoule formed of a frangible material and adapted to contain liquid to be applied; at least one hollow body defining an internal chamber adapted to receive at least one ampoule; a porous plug containing colorant, such that liquid flows through the porous plug when the ampoule is fractured and colorant is transferred to the liquid to be applied; and a porous pad secured to said body and closing off an open end thereof, such that the colored liquid flows through said porous pad.

By providing a liquid applicator in accordance with the present invention, numerous advantages are realized. For example, a user may use the application to apply a stable colored liquid. Further, colorant will not settle out of the liquid and cause non-uniform distribution of colorant in the liquid. This is important when it is employed to apply pre-operative liquid to indicate to the user where the liquid has been applied.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means, instrumentalities and combinations particularly pointed out in the appended claims.

BRIEF DESCRIPTION OF THE DRAWINGS

In the accompanying drawings which form a part of the specification and are to be read in conjunction therewith, and in which like reference numerals are employed to indicate like parts in the various views:

FIG. 5 is a perspective view of a liquid applicator constructed in accordance with an embodiment of the invention;

FIG. 6 is a side plan view of a liquid applicator constructed in accordance with an embodiment of the invention exposing the ampoules being fractured and the liquid flowing through the porous plug; and FIG. 7 is an exploded view of the vent located at the distance of an applicator constructed in accordance with an embodiment of the invention enclosed by line 7 in FIG. 5.

DETAILED DESCRIPTION

Figure 1:
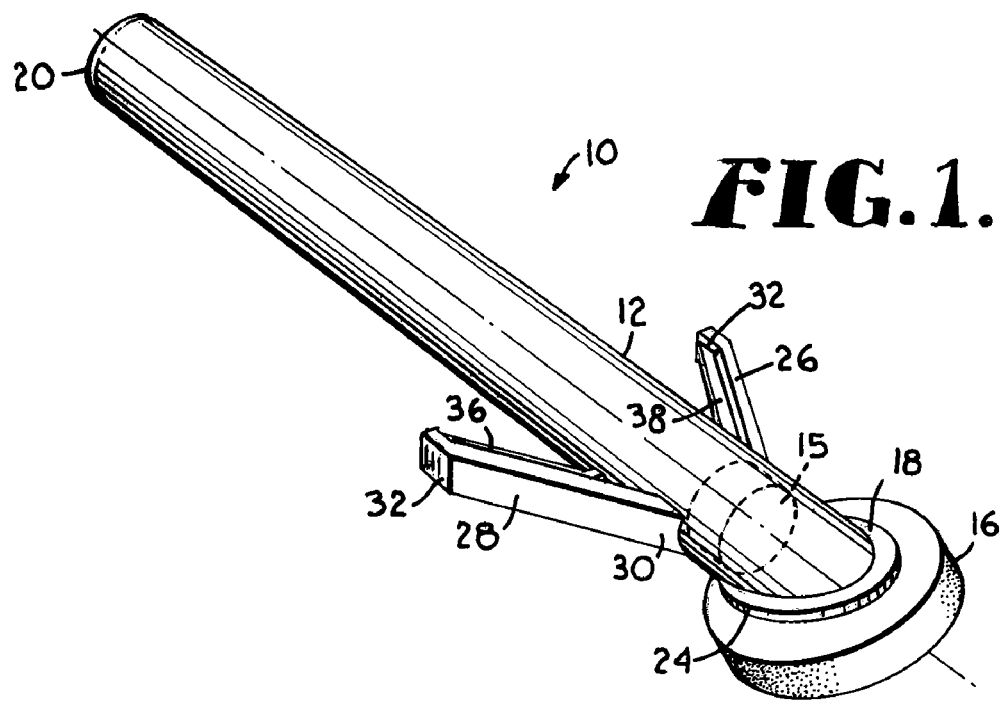
FIG. 1 is a perspective view of a liquid applicator constructed in accordance with an embodiment of the invention.

A liquid applicator for applying a desired colored liquid to a surface is provided. The applicator comprises a hollow body defining an internal chamber to receive at least one ampoule formed of a frangible material and containing the liquid to be applied. The liquid applicator further comprises at least one porous element containing colorant positioned such that upon fracturing at least one ampoule, the liquid flows though the porous element(s) containing colorant. Colorant is transferred to the liquid as it flows through the porous element containing colorant. The resulting colored solution may be applied to the desired surface.

The ampoule(s) may be used for containing various liquids such as medicaments, cleansing agents, cosmetics, polishes or the like. Further, it will be appreciated that the ampoule(s) may be numerous different shapes and sizes depending on the amount of liquid needed to be applied. For example, the applicator of the present invention may include long cylindrical ampoule(s) or may contain vial-type ampoule(s). Furthermore, more than one ampoule may be received by the body. Preferably, the ampoule(s) are formed of glass, although other materials are entirely within the scope of the present invention. The wall of the ampoules is of a thickness sufficient to contain the desired liquid during transport and storage, yet allow the ampoule to be fractured upon the application of localized pressure.

The body of the present embodiment of the invention may take many forms. The body has an internal chamber that is adapted to receive at least one ampoule. The body may also be shaped to hold multiple ampoules. In one form, the body is shaped to generally conform to the ampoule(s) contained within the body.

The porous element of the present invention also may take many forms. The porous element may be a porous plug and/or a porous pad. In other words, colorant may be contained in or on a porous plug located within the body of the applicator between the ampoule and an open end of the body. Colorant may be contained in or on a porous pad located at an open end of the body. The porous element is positioned such that when the ampoule(s) is fractured, the liquid flows through the porous element and colorant is transferred to the liquid to be applied. The porous element may be made of any porous material that allows liquid to flow through the material. The porous element may be, but is not limited to, a fabric, foam or a felt material. Colorant may be saturated throughout the porous element or colorant may be placed only on part of the element depending on the amount of colorant needed to achieve the desired color for the liquid.

Colorant may be a tint, pigment, dye, paint or any other substance that imparts or changes a hue of a liquid. For example, F D & C colorants may be used with the present embodiment of the invention. Furthermore, any combination of colorants may be used.

The ampoule(s) contained within the body of the applicator may be broken by any method known to those skilled in the art. These include, but are not limited to, squeezing the walls of the body inwardly to break the ampoule(s), using a lever or other mechanism to break the ampoule(s), or utilizing projecting wings with tappets as described below.

EXAMPLE 1

Figure 2:
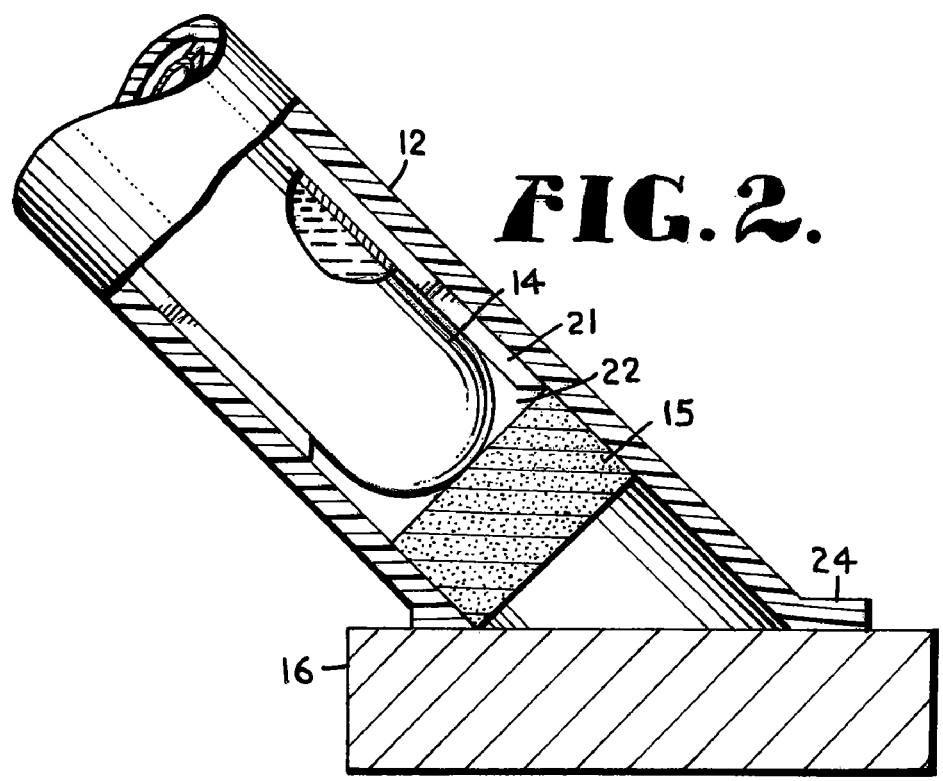
FIG. 2 is a side plan view of a liquid applicator constructed in accordance with an embodiment of the invention with a portion of the applicator body removed to expose the ampoule and the porous plug.

Referring to the drawings in general and initially to FIG. 1 and FIG. 2 in particular, where like reference numerals identify like elements in the various views, a liquid applicator manifesting aspects of the invention is illustrated and designated generally by the numeral 10. The liquid applicator 10 generally includes a body 12, at least one closed ampoule for containing liquid 14 received in the body 12, and porous pad 16 secured to body 12. In the illustrated embodiment, the liquid applicator 10 also includes a porous plug 15 that contains colorant.

In the illustrated embodiment, the ampoule 14 contains an antiseptic solution to be applied to a patient's skin prior to surgery. The antiseptic used in the illustrated embodiment is chlorohexadine gluconate. However, any liquid may be used with the liquid applicator of the embodiment of the present invention. The ampoule 14 is illustrated as an elongated cylinder, which defines a central longitudinal axis. However, it will be appreciated that the principles of the present invention also may be applied to spherical or elongated polygonal ampoules. Preferably, the ampoule 14 is formed of glass, although other materials are entirely within the scope of the present invention.

In the illustrated embodiment, body 12, is of a generally hollow cylindrical shape and includes axially opposed first and second ends 18, 20 and presents a central longitudinal axis "x". The proximal first end 18 is open and the distal second end 20 is closed. The illustrated body 12 is formed of high-density polyethylene, although any material exhibiting similar flexibility and integrity may be used in the illustrated embodiment, the second end 20 is closed during the molding process obviating the need for a cap or the like. However, the second end may be open or may be closed using a cap. The illustrated body 12 is elongated and defines a central longitudinal axis, which is collinear with the central longitudinal axis of the ampoule 14. Preferably, the thickness of the wall is between 0.012-0.150 inches. More preferably, the thickness of the wall is approximately 0.050 inches.

Figure 4:
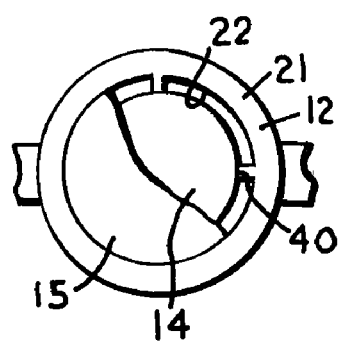
FIG. 4 is a fragmentary cross-sectional view taken generally across line 4-4 of FIG. 3.

Body 12 includes an interior wall 21, which defines an internal chamber 22 within body 12. Interior wall 21 is shaped to conform generally with the shape of the ampoule 14, which is received within the internal chamber 22. With reference to FIG. 4, the circumference of the interior wall 21 is slightly larger than the outer surface of the ampoule body such that a plurality of inwardly projecting ridges 40 positioned on the interior wall 21 of the hollow body 12 supports the ampoule 14 therein. Preferably, the interior wall 21 includes four inwardly projecting ridges 40, which are offset from one another by approximately 90 degrees around the interior wall 21 of body 12. The ridges 40 engage the periphery of the ampoule to maintain the ampoule 14 within the internal chamber 22 and prevent untoward movement of shards of the ampoule through the porous pad 16 when fracturing of the ampoule is affected, as more fully described below.

Referring again to FIG. 1 and FIG. 2, body 12 further presents a flange 24 protruding from the open end 18 along the periphery thereof. In the illustrated embodiment, the flange 24 is continuously molded to the body 12 and is disposed at an angle of 45 degrees, with respect to the central longitudinal axis of the body. The flange 24 is adapted to support the porous pad 16, as more fully described below.

Body 12 also includes a pair of elongated gripping members 26, 28 which are diametrically opposed and project from the body. Each gripping member 26, 28 include an attachment portion 30 outwardly extending from the body 12 and a handling portion 32 extending from the distal end of the attachment portion 30.

Body 12 also includes structure for fracturing the ampoule 14. In the illustrated embodiment, the structure includes breaking tabs or tappets 36, 38 interposed between the gripping members 26, 28 and the body 12. Upon depression of the gripping members 26, 28, the breaking tabs 36, 38 flex the body 12 inwardly, thereby localizing the forces effected by squeezing the members 26, 28 toward one another and enhancing fracturing of the ampoule 14 as more fully described below. It will be appreciated, however, that the principles of the present invention are equally applicable to various other structures and methods for fracturing the ampoule 14.

In the illustrated embodiment, the liquid applicator 10 of the present invention is constructed to house a 6.0 ml or 10.5 ml ampoule. It will be understood and appreciated, however, that various numbers of ampoules and ampoules of various sizes may be utilized and such is contemplated to be within the scope of the present invention.

In the illustrated example, a porous pad 16 such as a sponge or the like closes off the open end 18 of the body 12. The porous pad 16 is received on flange 24 and encloses the ampoule 14 within the internal chamber 22. The porous pad 16 is disposed at angle 45 degrees with respect to the central longitudinal axis of the body 12. Thus, the liquid may be released to flow by gravity upon fracture of the ampoule 14 to the porous pad 16 affixed to the open end 18 of body 12.

The porous pad 16 is formed of felt or an open-celled foam material that is laminated on one side with a laminate material. The laminated felt material used in the illustrated embodiment was Novonnete®SP-64 (3905) Polyester (Non-Woven) was laminated to 0.360"±0.032" SIF-# 3-1000Z felt, (Natural Color Non-Pigmented) Reticulated Polyester Urethane. The laminate material may also be a woven or non-woven polyester material such as polyethylene. The laminate material of the porous pad 16 is positioned between the open-celled foam material and the flange 24 of the body 12. By employing a porous pad having a laminate as described herein, numerous advantages are realized. For example, the material presents a physical barrier that resists puncture by glass fragments of the fractured ampoule. Further, the laminate material also increases the bond strength of pad 16 to body 12.

The illustrated porous pad 16 is cut from a sheet of sponge material having the desired porosity for the liquid to be dispensed, whereby liquid is prevented from flowing immediately through the pad 16 when the ampoule 14 is fractured. In other words, once an ampoule 14 is fractured, the released liquid saturates porous plug 15 and then saturates pad 16 and flows from pad 16 only as the surface absorbs the liquid from the saturated pad 16. Consequently, the body 12 essentially functions as a reservoir of the desired liquid. The porous pad 16 is preferably generally circular in shape although it will be appreciated that the pad may be of any desired size and shape, which is capable of being supported on the flange 24.

In the illustrated embodiment, porous plug 15 is positioned between porous pad 16 and ampoule 14. Porous plug 15 may be any porous material. In the illustrated embodiment, the porous plug is an open-celled foam material or felt, preferably, Novonnete® SP-64 (3905) Polyester (Non-Woven) was laminated to 0.360"±0.032"-# 3-1000Z felt, (Natural Color Non-Pigmented) Reticulated Polyester Urethane. The diameter of porous plug 15 is approximately 0.709 inches. Porous plug 15 helps control the rate liquid flows from the body and prevents shards of glass from pushing through porous pad 16 during use of the applicator. Porous plug 15 is cut from a sheet of foam or felt material having the desired porosity for the liquid to be dispensed. In the illustrated embodiment, colorant is contained with the porous plug. Further, in the illustrated embodiment the colorant contained in the porous plug was CAS No. 2353-45-9 FD&C Green #3 dye. The porous plug containing colorant utilized in the illustrated embodiment was prepared using the method described in Example 3

During formation of the applicator, the ampoule 14 is inserted into the internal chamber 22 of the body 12. Thereafter, the porous plug 15 is inserted into the internal chamber of the body 12 between ampoule 14 and flange 24. Then the porous pad 16 is secured to the body 12 of the applicator by welding the laminate material to the flange 24 using an ultrasonic welding operation. The polyester material of the laminate provides suitable welding material that melts together with the material of the flange 24 to secure the porous pad 16 in place over the internal chamber 22 and enclose the ampoule 14. Securing the porous pad 16 on the flange 24 in this manner facilitates preventing leakage between the flange 24 and the pad 16. It will be appreciated that other suitable securing expedients could be employed in place of the ultrasonic welding operation. For example, the porous pad 16 could be secured in place by an adhesive or stitching, or by heat sealing or chemically bonding the pad in place. Such alternative securing expedients are contemplated to be within the scope of the present invention.

Figure 3:
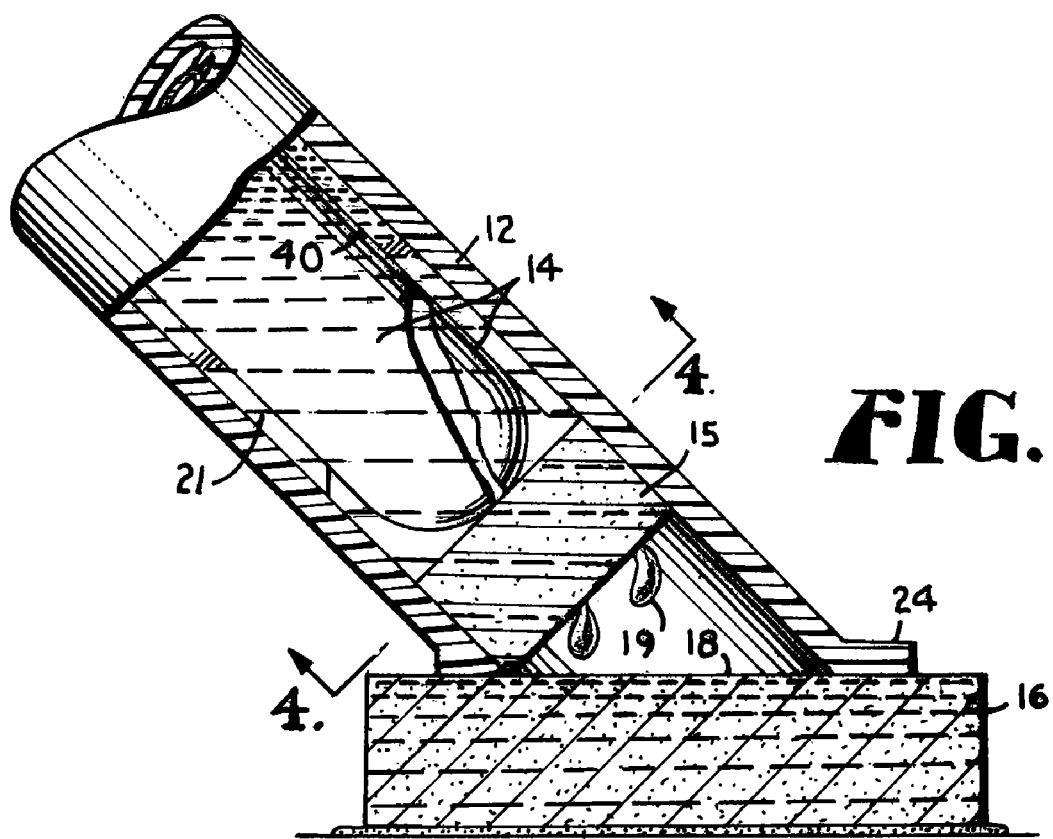
FIG. 3 is a side plan view of a liquid applicator constructed in accordance with an embodiment of the invention exposing the ampoule being fractured and the liquid flowing through the porous plug.

With reference to FIGS. 1, 2 and 3, in use, the applicator 10 presents a hand-held liquid applicator that is squeezed to release the desired liquid contained therein for application to a surface. The applicator 10 is designed to be grasped by the user so that the gripping members 26, 28 are held between the thumb or palm and fingers of one hand of the user, thus allowing for single-handed operation. The ampoule 14 is fractured by the user squeezing the gripping members 26, 28 toward one another. The movement of the members 26, 28 is transferred by the tabs 36, 38 to the body 12 to deform the body 12 inwardly and exert discrete localized fracturing forces against the ampoule 14. The gripping members provide a lever action that gains mechanical advantage as the members are squeezed toward one another. Accordingly, if the user has limited gripping strength, or if the wall of the ampoule is exceptionally thick, the members ensure fracturing of the ampoule.

As shown in FIG. 3, once the members 26, 28 have been sufficiently squeezed together, the resulting forces fracture the ampoule 14 releasing the liquid contained therein. Once ampoule 14 is fractured, body 12 essentially functions as a reservoir of the desired liquid. The released liquid under the force of gravity flows down body 12, through porous plug 15 saturating the porous plug 15 which contains colorant. Consequently, the liquid flows through the porous plug 15 and colorant is transferred to the liquid. The colored liquid 19 then flows through open end 18 and through porous pad 16 which may also contain colorant. As the liquid flows through the porous pad 16, colorant is transferred from the pad to the liquid. Thereafter, application of the colored liquid 19 is accomplished by bringing porous pad 16 into contact with the desired surface. The user may then use a painting or scrubbing motion to apply the liquid to the surface. The entire process of fracturing ampoule 14 and applying the liquid to a desired surface is achieved with the use of only one hand of the user.

EXAMPLE 2

With reference FIG. 5 and FIG. 6, in particular, where like reference; numerals identify like elements in the various views, an embodiment of the liquid applicator is illustrated and designated generally by the numeral 41. Liquid applicator 41 generally includes a body 42, and a porous pad 44 secured to flange 46 of body 42 and a lever 48.

Two ampoules 50 and 52 are received in body 42. The liquid applicator 41 is constructed to house two 13 ml ampoules. The thickness of the walls of the 13 ml ampoules is about 0.3 mm. However, ampoules of various sizes may be used. Ampoules 50 and 52 may be used for containing various liquids such as medicaments, cleansing agents, cosmetics, polishes or the like. In the illustrated embodiment, ampoules 50 and 52 contain antiseptic solution to be applied to a patient's skin prior to surgery. Ampoules 50 and 52 are illustrated as elongated cylinders with a central longitudinal axis. However, it will be appreciated that the principles of the present invention also may be applied to spherical or elongated polygonal ampoules. Furthermore, it will be appreciated that the principles of the present invention may be applied to more than two ampoules.

Preferably, ampoules 50 and 52 are formed of glass, although other materials are entirely within the scope of the present invention. In the illustrated embodiment, ampoules 50 and 52 are placed side by side within body 42. The wall of glass ampoules 50 and 52 is of a thickness sufficient to contain the desired liquid during transport and storage, yet allow ampoules 50 and 52 to be fractured upon the application of localized pressure.

Body 42 is generally hollow and oval or elliptical in shape and includes axially opposed first and second ends 54, 56. The proximal first end 54 is open and distal second end 56 is closed with cap 58. Illustrated body 42 is formed of high-density polyethylene, although any material exhibiting similar flexibility and integrity may be used. In the illustrated embodiment, body 42 and cap 58 were molded with 100% virgin material DOW, HDPE, Resin # 12454N, as defined in FDA Master File Number 4251. In the preferred embodiment, second end 56 is closed with cap 58, however second end may also be closed during the molding process obviating the need for a cap or the like.

Body 42 includes an interior wall 60 which defines an internal chamber 62 within body 42. Interior wall 60 is shaped to conform generally with the shape of ampoules 50 and 52 which are received within internal chamber 62. The circumference of interior wall 60 is slightly larger than the outer surface of the two ampoule bodies. Dividing wall 64 of hollow body 42 separates ampoules 50 and 52 and maintains ampoules 50 and 52 within internal chamber 62. Illustrated body 42 is elongated and defines a central longitudinal axis "x".

The thickness of the wall of the applicator may be between 0.040 to 0.080 inches and preferably is approximately 0.060 inches, except thin wall 66. The thickness of the wall of body 42 is reduced around crush area 64. Thin wall 66 may be between 0.020 to 0.040 inches and preferably is 0.030 inches. However, it will be appreciated that different wall sizes may be used within the scope of the embodiment of the invention. Thin wall 66 makes it easier for crush portion 68 of lever 48 to fracture multiple ampoules when lever 48 is depressed. This will be discussed in more detail later.

Body 42 further presents a flange 46 protruding from proximal end 54 along the periphery thereof. In the preferred embodiment, flange 46 is continuously molded to body 42 and is disposed at an angle. Preferably, flange 46 is disposed an angle of 45°, with respect to the central longitudinal axis of the body. It will be appreciated that flange 46 may be disposed at a variety of angles with respect to the central longitudinal axis of body 42. Flange 46 is adapted to support porous pad 44, as more fully described below.

Porous pad 44, such as a sponge or the like, closes off open end 54 of body 42. Porous pad 44 is received on flange 46 and encloses ampoules 50 and 52 within internal chamber 62. Porous pad 44 may be formed of felt or an open-celled foam material. In the illustrated embodiment, porous pad 44 was formed of SIF-# 3-1000Z felt, (Natural Color Non-Pigmented) Reticulated Polyester Urethane.

Porous pad 44 is cut from a sheet of foam or felt material having the desired porosity for the liquid to be dispensed. Porous pad 44 is preferably generally square in shape although it will be appreciated that the pad may be of any desired size and shape which is capable of being supported on flange 46.

In the illustrated embodiment, a woven or non-woven laminate material is laminated to porous pad 44. The material laminate material may be a woven or non-woven polyester material. In the illustrated embodiment, Novonnete® SP-64 (3905) Polyester (Non-Woven) was laminated to 0.360"±0.032" SIF-# 3-1000Z felt, (Natural Color Non-Pigmented) Reticulated Polyester Urethane. The laminate material is positioned between porous pad 44 and flange 46 of body 42. As such, the laminate material functions to prevent shards of glass from the fractured ampoules from pushing through the porous pad during use of the applicator. The laminate material also provides a suitable welding material for securing the porous pad in place on the body when an ultrasonic welding operation is used to manufacture the applicator.

In the illustrated embodiment, porous plug 70 is positioned between porous pad 44 and ampoules 50 and 52. Porous plug 70 may be an open-celled foam material or felt. In the illustrated embodiment, Novonette SP-64 (3905) Polyester (Non-Woven) was laminated to 0.360"±0.032"SIF-#3-1000Z Felt, (Natural Color Non-Pigmented) Reticulated Polyester Urethane. Porous plug 70 helps control the rate liquid flows from the body and prevents shards of glass from pushing through porous pad 44 during use of the applicator. Porous plug 70 is cut from a sheet of foam or felt material having the desired porosity for the liquid to be dispensed. In the illustrated embodiment, colorant is contained with the porous plug. Further, in the illustrated embodiment the colorant contained in the porous plug was CAS No. 2353-45-9 FD&C Green #3 dye. The porous plug containing colorant utilized in the illustrated embodiment was prepared using the method described in Example 3.

Body 42 also includes a lever 48 projecting from the top portion of body 42. However, it will be appreciated that lever 48 may project from any portion of body 42. Lever 48 is any mechanism for fracturing more than one ampoule at substantially the same time. Lever 48, includes hinge portion 72, crush portion 68 and handling portion 74 extending from the distal end of lever 48. Preferably, lever 48 extends outwardly from body 42 at an angle of between 20° and 40° with respect to the central longitudinal axis of body 42. More preferably, lever 48 extends from body 42 at approximately 27° with respect to the central longitudinal axis "x" of body 42. It will be appreciated that lever 48 may be disposed at a variety of angles with respect to the central longitudinal axis of body 42.

In the illustrated embodiment, lever 48 is continuously molded with body 42. It will be understood and appreciated, however, that separately formed levers are contemplated to be within the scope of the present invention.

Handling portion 74 of lever 48 of the illustrated embodiment is spaced between 0.5 and 1.5 inches from body 42. Preferably, handling portion 74 is spaced approximately 1.0 inch from body 42. Handling portion 74 of lever 48 includes a textured outer surface to facilitate handling of applicator 41 and to inhibit slippage from the user's hand during application.

In the illustrated embodiment, lever 48 includes crush portion 68 and hinge portion 72 attached to body 42. It will be appreciated, however, that the principles of the present invention are equally applicable to various other structures for fracturing ampoules 50 and 52, such as multiple crush portions, multiple hinge portions and a crush portion that may be attached or detached to body 42. Handling portion 74 of lever 48 presents a gripping area which is significantly larger than the area of crush portion 68. Upon depression of lever 48, crush portion 68, flexes body 42 inwardly at thin wall 66, thereby localizing the forces effected by depressing lever 48 toward body 42 and enhancing fracturing of ampoules 50 and 52 as more fully described below.

Several features of lever 48 of the illustrated embodiment enhance the ability to fracture at least two ampoules at the same time including: the thickness of lever 48, the curvature of lever 48, support rib 76, the thickness of hinge portion 72 and the width of crush portion 68. The thickness of lever 48 is approximately 0.080 to 0.15 inches and preferably is 0.11 inches. In the illustrated embodiment, lever 48 is approximately 2.35 inches long. Hinge portion 72 of the illustrated embodiment is thinner than the rest of lever 48. Hinge portion 72 is approximately 0.040 to 0.080 inches thick, preferably 0.060 inches thick. The curvature of lever 48 and support rib 37 increase the leverage of handling portion 74 of lever 48 making it easier for the user to fracture two ampoules substantially simultaneously.

The ratio of the width of crush portion 68 to the width of ampoules 50 and 52 side by side is important with respect to reliable breakage of ampoules 50 and 52. In the illustrated embodiment, the width of the crush portion 68 had to be at least approximately ⅕ the width of the two ampoules side by side to produce breakage of the ampoules almost simultaneously. The width of the two ampoules side by side was approximately 1.03 inches. The minimum width of the crush portion of the lever that produces breakage of the ampoules almost simultaneously was 0.200 inches. Thus, a length aspect ratio for reliable ampoule break was 1.03/0.200 or 5.15. All of these features, either singularly or in combination, along with thin wall 66, help enhance the ability of the lever to break multiple ampoules at the same time.

With reference to FIG. 7, vent 80 of the illustrated embodiment is shown. Vent 80 is located at distal end 56 of body 42. Vent 80 is a small cut out portion of body 42 allowing air to flow from internal chamber 62 of body 42 to the outside of body 42 and vice versa. This is accomplished by a small cut out portion of body 42 starting on the outside of body 42, going over the lip of body 42 and continuing inside body 42. Internal cut out portion 82, external cut out portion 84 and cut out lip 86 allow air to flow in and out of internal chamber 62 of body 42 underneath cap 58. Cap 58 entirely seals off internal chamber 62 except for cut out vent 80.

Restraint element 78 is positioned between ampoules 50 and 52 and porous plug 70. Restraint element 78 allows liquid to flow from body 42, through porous plug 70 and into porous pad 44. Restraint element 78 restrains ampoules 50 and 52 in a position to facilitate proper breaking. Restraint element 78 holds the ends of ampoules 50 and 52 near crush point 64 so that the ends of ampoules are properly broken and do not restrict the flow of liquid. Restraint element 78 may take a variety of shapes depending on the type of liquid to be applied. In the illustrated embodiment, restraint element 78 has two fan-shaped openings.

In use, applicator 41 presents a hand-held liquid applicator wherein lever 48 is depressed to release the desired liquid contained within ampoules 50 and 52 therein for application to a surface. Applicator 41 of the illustrated embodiment is grasped by one hand of a user. The bottom of body 42 is grasped with the palm and fingers of user, the user's fingers wrap around the bottom and side of the body 42 so the tips of the user's fingers rest on the top of body 42. The thumb of the same hand is positioned on handling portion 74 of lever 48 allowing for single-handed operation. The user depresses lever 48 toward body 42 to fracture ampoules 50 and 52. The movement of lever 48 is transferred by crush portion 68 to thin wall 66 of body 42 to deform body 42 inwardly and exert discrete localized fracturing forces against ampoules 50 and 52. Lever 48 provides an action that gains mechanical advantage as lever 48 is depressed toward body 42. Accordingly, if the user has limited gripping strength, or if the wall of the ampoule is exceptionally thick, the lever ensures fracturing of the ampoules.

Once lever 48 has been sufficiently depressed, the resulting forces fracture ampoules 50 and 52 almost simultaneously, thus releasing the liquid contained in each ampoule. The released liquid under the force of gravity flows down body 42, saturating porous plug 70 which contains colorant. Consequently the liquid flows through porous plug 70 and colorant is transferred to the liquid. The colored liquid 90 flows through open end 54 and through porous pad 44. Thereafter, application of the colored liquid 90 is accomplished by bringing porous pad 44 into contact with the desired surface. Thereafter, application of the liquid is accomplished by bringing porous pad 44 into contact with the desired surface. The user may then use a painting or scrubbing motion to apply the liquid to the surface. The entire process of fracturing ampoules 50 and 52 and applying the liquid to a desired surface is achieved with the use of only one hand of the user

EXAMPLE 3

In this example, colorant is contained in the porous plug of the applicator. The illustrated example was done for both 10.5 mL porous plugs and 26 mL porous plugs. The material used for the porous plug was Novonette SP-64 (3905) Polyester (Non-Woven) Laminated to 0.320 inchest +/−0.030 inches open cell, (Natural Color Non-Pigmented) Polyester Urethane Reticulated Foam 80-100 PPI. The diameter of the 10.5 mL porous plug was 0.709 and its thickness was 0.023 inches. The size of the 26 mL porous plug was 1.06 inches ×0.57 inches and it had a thickness of 0.023 inches. The equipment used included a 5 gallon nalgene carboy container with pouring spout, air motor, 3" stainless steel shaft, 3" folding blade mixing propeller, and a Metek digital tachometer—Model 1726 to measure shaft RPM.

Colorant is added to the porous plugs using the following method. First, the tint to alcohol ratio (grams of tint/grams of 70% isopropyl alcohol (IPA)) was determined to ensure a consistent color shade when applied to the treatment area. The following calculations were use to determine the tint to alcohol ratio:

$$5 \text{ gallons of } 70\% \ IPA = \frac{5 \text{ Gal.}}{1} \times \frac{3785.412 \text{ mL}}{1 \text{ Gal.}} \times \frac{0.879 \text{ grams}}{\text{mL}}$$

$$= 16{,}637 \text{ grams of } IPA$$

$$\frac{\text{Grams of green \#3}}{16{,}637 \text{ grams of } IPA} \rightarrow \text{grams of green \#3} = 16{,}637 \text{ gr. } IPA \times 0.00375$$

$$= 62.39 \text{ gr. of green \#3}$$

The tint to alcohol ratio for consistent color with CAS No. 2353-45-9 FD&C Green #3 dye was approximately 0.00375.

Five (5) gallons of 70% IPA (16.64 Kg) was added to the five (5) gallon carboy container. Then 62.4 grams of CAS No. 2353-45-9 FD&C Green #3 dye was added to the five (5) gallons of 70% IPA. The carboy container was placed onto a cart containing an air motor fixture. The air motor was dropped down and secured to the fixture while the shaft and propeller were centered through the carboy opening. The solution was mixed with a shaft rotation of 500 rmp for thirty (30) minutes to ensure total dissolution of the dye into the 70% IPA.

After the dye had thoroughly dissolved into 70% IPA, the safety dispensing jug was removed from the mixer apparatus and closure cap was tightened. The solution was poured into a tank with a corresponding dipping basket. The porous plugs were placed into a dipping basket and lowered into the tank. Solution was added as necessary until porous plugs were completely saturated in dyed solution. The dipping basket was removed from the tank and excess solution was drained. The wet porous plugs were placed onto surface covered with plastic to dry for 24 hours.

Thirty random porous plug samples were obtained and their individual wet weights were recorded and analyzed with the aid of MINITAB statistical analysis software package. As may be seen in the results below, the average wet weight was about two (2) grams, while the lowest weight measured was close to 1.8 grams and the highest was 2.1 grams. The following Tables 1, 2 and 3 list the properties of the tinted porous plugs of the present example.

TABLE 1

| Process Data | |
|---|---|
| USL (Upper Specification Limit) | 2.2500 |
| LSL (Lower Specification Limit) | 1.7500 |
| Mean | 2.0061 |
| Sample Number | 30 |
| Standard Deviation (Within) | 0.0825230 |
| Standard Deviation (Overall) | 0.0816697 |

Constructed and operated as previously described, this invention provides a liquid applicator and a method of coloring a liquid. More specifically, the present invention relates to a liquid applicator having a flexible hollow body within which a liquid-filled, glass ampoule is received. The liquid applicator also has porous element having colorant closing off an open end of the body. When the ampoule is fractured, the liquid flows through the porous element having colorant. Colorant is transferred to the liquid as it flows through the porous element having colorant. The resulting colored solution may be applied to the desired surface.

From the foregoing, it will be seen that this invention is one well adapted to attain all the ends and objects hereinabove set forth together with other advantages which are obvious and which are inherent in the structure. It will be understood that certain features and subcombinations are of utility and may be employed without reference to other features and subcombinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

The invention claimed is:

1. An applicator for applying a colored antiseptic solution to a desired surface, the applicator comprising:
    antiseptic solution in an amount sufficient to be applied to a desired surface and to have an antimicrobial effect on the desired surface, the antiseptic solution comprising chlorhexidine gluconate; and
    at least one porous element containing colorant, wherein at least some of the colorant is transferred to the antiseptic solution when the antiseptic solution contacts the at least one porous element.

2. The applicator of claim 1, wherein the at least one porous element is one of a foam or felt material.

3. The applicator recited in claim 1, wherein the colorant changes the hue of the antiseptic.

4. The applicator recited in claim 1, wherein the colorant adds hue to the antiseptic.

5. The applicator recited in claim 1, wherein the colorant is one of a tint, dye, pigment or paint.

6. The applicator according claim 5, wherein the colorant is a dye.

7. The applicator according to claim 6, wherein the dye is an FD&C dye.

8. The applicator of claim 1, wherein the porous element is imbibed with the colorant.

9. The applicator of claim 1, wherein the colorant is located on the surface of the porous element.

10. The applicator of claim 1, wherein the at least one porous element is saturated.

11. A method for applying a colored antiseptic solution to a desired surface, the method comprising:
    providing an antiseptic solution in an amount sufficient to be applied to a desired surface and to have an antimicrobial effect on the desired surface, the antiseptic solution comprising chlorhexidine gluconate;
    contacting the antiseptic solution with at least one porous element containing colorant such that at least some of the colorant is transferred to the antiseptic solution; and
    applying the colored antiseptic solution to the desired surface.

12. The method of claim 11, wherein the colorant changes the hue of the antiseptic.

13. The method of claim 11, wherein the colorant adds hue to the antiseptic.

14. The method of claim 11, wherein the colorant is one of a tint, dye, pigment or paint.

15. The method of claim 14, wherein the colorant is a dye.

16. The method of claim 15, wherein the dye is an FD&C dye.

17. The method of claim 11, wherein the porous element is imbibed with the colorant.

18. The method of claim 11, wherein the colorant is located on the surface of the porous element.

19. The method of claim 11, wherein the at least one porous element is one of a foam or felt material.

20. The method of claim 11, wherein the at least one porous element is saturated.

* * * * *